United States Patent [19]

Grams

[11] 4,244,377
[45] Jan. 13, 1981

[54] EAR PROBE FOR USE IN CLOSED-LOOP CALORIC IRRIGATION

[76] Inventor: Guenter A. Grams, 2443 Norse Ave., Costa Mesa, Calif. 92627

[21] Appl. No.: 952,690

[22] Filed: Oct. 19, 1978

Related U.S. Application Data

[63] Continuation-in-part of Ser. No. 760,178, Jan. 17, 1977, abandoned.

[51] Int. Cl.³ .................... A61B 5/00; A61B 10/00
[52] U.S. Cl. .................... 128/742; 128/746; 128/401; 128/151
[58] Field of Search .......... 128/746, 742, 344, 349 B, 128/349 BV, 399–401; 46/87, 151

[56] References Cited

U.S. PATENT DOCUMENTS

| | | | |
|---|---|---|---|
| 726,009 | 4/1903 | Whisler | 46/87 |
| 824,071 | 6/1906 | Faber et al. | 46/87 |
| 2,190,384 | 2/1940 | Newman | 128/400 |
| 2,826,000 | 3/1958 | Fischman et al. | 46/87 |
| 3,049,125 | 8/1962 | Kriwkowitsch | 128/344 |
| 3,848,607 | 11/1974 | St. Clair | 128/400 |
| 4,102,342 | 7/1978 | Akiyama et al. | 128/344 |

FOREIGN PATENT DOCUMENTS

187217 10/1966 U.S.S.R. .................... 128/742

OTHER PUBLICATIONS

Foti, Thos. et al., "A Closed Flow Water Caloric System", JNMA vol. 69 No. 5, 6/77 pp. 303–305.

Ono, H. et al., "A New Caloric Tester Using an Ear Canal Balloon", Revue de Laryngologie, Otologie and Rhinologie, vol. 97, Nos. 5–6, May-Jun. 1976 pp. 223–230.

*Primary Examiner*—Robert W. Michell
*Assistant Examiner*—Francis J. Jaworski
*Attorney, Agent, or Firm*—Philip M. Hinderstein

[57] ABSTRACT

An ear probe for use in closed-loop caloric irrigation including a manifold and balloon, the manifold conducting fluid flow into and out of the balloon concentrically, the balloon being a one-piece, elongate, cylindrical member formed from an elastic material and having open and closed ends and sections of different diameters and thicknesses. One section is inflatable, having a small diameter and a minimum thickness to permit insertion into the ear canal and inflation into contact with the inner ear. Another section has a relatively large outside diameter and a substantial thickness so as to contact the exterior ear and limit movement of the balloon into the ear canal. An intermediate section has a relatively small diameter to permit insertion into the ear canal and an increased thickness to prevent inflation thereof, the intermediate section providing a return flow channel for fluid conducted through the balloon.

11 Claims, 4 Drawing Figures

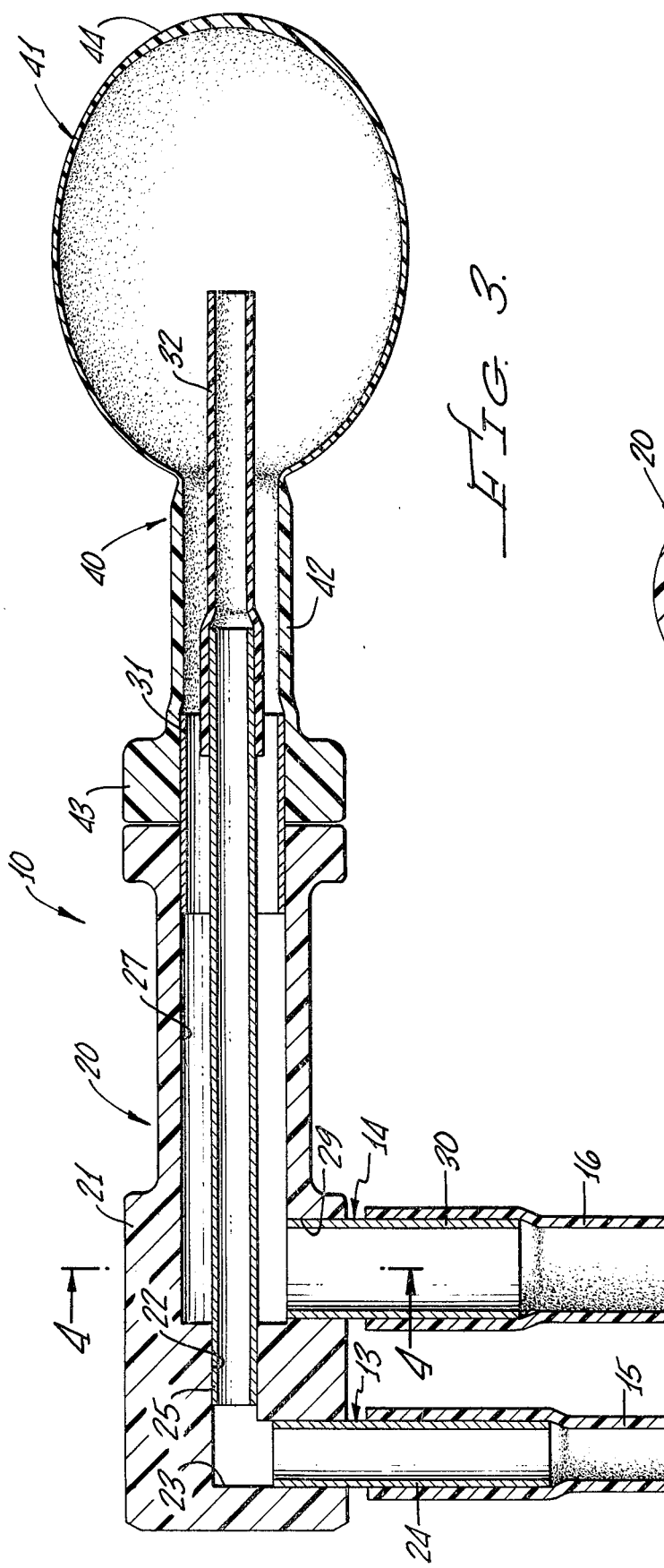
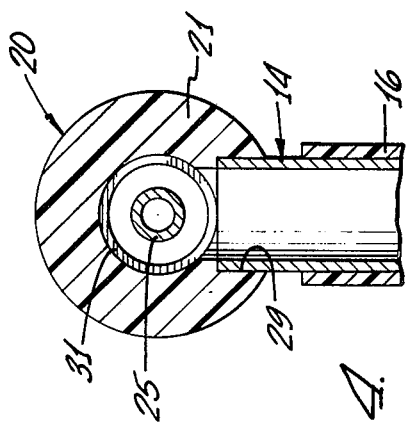

EAR PROBE FOR USE IN CLOSED-LOOP CALORIC IRRIGATION

CROSS-REFERENCE TO RELATED APPLICATION

This application is a continuation-in-part of application Ser. No. 760,178, filed Jan. 17, 1977 now abandoned.

BACKGROUND OF THE INVENTION

1. Field of the Invention

The present invention relates to an ear probe for use in closed-loop caloric irrigation and, more particularly, to an improved probe including a disposable silicone rubber balloon for use with caloric irrigation apparatus.

2. Description of the Prior Art

The human species has evolved and developed an elaborate balance system to allow for proper relationship between its surroundings and an erect posture. The system is a complicated one, requiring integration of information from the visual system, the vestibular system, and the skeletal-muscular system.

For a patient complaining of dizziness and impaired balance, a disorder can exist in any of these systems. To determine the source of the disorder, many different tests are performed. In addition to the spontaneous nystagmus and postual reflex tests, a complex recording technique has been developed called electronystagmography (ENG). ENG provides for a permanent objective recording, obtained in a relatively standardized manner, of responses from the vestibular system.

In order to perform adequate tests utilizing ENG, the vestibular system must be stimulated to create the condition of dizziness and impaired balance. It has been determined that proper stimulation may be achieved by adding heat to or taking heat away from the inner ear. It is for this purpose that several caloric irrigators have been developed.

A conventional caloric irrigator consists of a fluid reservoir, a fluid pump, a heating and cooling system, and a conduit for conducting fluid, pumped by the pump, from the reservoir, through the heating and cooling system, to a probe insertible into the ear canal. While caloric irrigators are widely used, existing equipment has many disadvantages associated therewith. A basin or towel is required to catch the water flowing out of the ear, making the procedure difficult and awkward. The procedure requires trained personnel and it is virtually impossible to stimulate both ears simultaneously, which many experts say is a necessity for a meaningful test. Such a procedure is not applicable in the case of a patient with a perforated eardrum since the water will flow through the perforation. It is also difficult to measure a fixed stimulation parameter such as temperature, fluid volume, and flow rate.

To solve the above problems, it has been proposed by researchers in the Department of Otorhinolaryngology, School of Medicine, Keio University, Tokyo, Japan, to provide a closed-loop channel for conducting fluid from the reservoir to the ear and back to the reservoir. The proposed system consists of a water tank with a stirrer, a heating and cooling system, a temperature control system, a pump system with a timer, and a silicone ear canal balloon. The silicone balloon is inserted into the auditory canal and is made to adhere tightly to the canal wall by the pressure of the water as it is pumped from the reservoir, into the balloon, and back to the reservoir. Heat transfer to the ear canal is achieved through the wall of the balloon. Since the water does not directly contact the ear, the system can be used even with a perforated eardrum. Unilateral or bilateral simultaneous stimulation can be performed and the various parameters can be readily controlled.

Even with the above advantages of a system using an inflatable balloon, several problems still exist with the proposed apparatus. The balloon of the proposed system is a one-piece, molded part having an inlet and an outlet that are positioned side by side. This makes the balloon overly large, preventing its use with very small or partially obstructed ear canals. Furthermore, the one-piece construction is complex and expensive and the entire unit must be replaced periodically.

Generally speaking, the purpose of a probe is to maintain a precise temperature, for a given time, in the ear canal, as close to the ear drum as possible. Ear canals vary in size depending on age and physical structure of a patient so it is necessary to construct a probe that can be used in all subjects, thereby eliminating error by a technician. To maintain a given temperature in the ear canal, it is necessary to maintain a given fluid flow. Since the dimensions should be held to a minimum and flow to a maximum, the construction of a total probe is the key to feasibility.

The ear canal is sensitive to foreign objects. Therefore, the probe must be soft and of low mass so that placement can be done with the least amount of trauma to the patient. For sterilization purposes, the portion of the probe that goes into the ear should be replaceable. The probe construction should define probe placement relative to the ear so that tests are repeatable. Repeatability of probe placement in the ear canal is also important because total heat transfer is dependent on balloon contact. A probe satisfying all of these requirements has been unavailable heretofore.

SUMMARY OF THE INVENTION

According to the present invention, these problems are solved in a manner unknown heretofore by the provision of a unique ear probe for use in a closed-loop caloric irrigator. The present probe includes a manifold and an inflatable balloon adapted to be placed in the ear canal and to have a fluid such as water pumped therethrough for stimulating the ear canal wall and the ear canal. With the present probe, the fluid flow into and out of the balloon is concentric. This allows the tip of the probe to have an extremely small diameter, providing greater applicability with individuals with small or partially obstructed ear canals. The probe is not only smaller, but simpler and less costly than prior probes, permitting replacement of the balloon only and not the entire probe. Use of a concentric in-flow and out-flow system also prevents partial collapse of the balloon because of the ear creating a restriction.

The present probe is soft and of low mass so that placement can be done with the least amount of trauma to a patient. The hoses leading to the probe are small and lightweight and are attached to a right angle to the probe to assure a minimal total mass to be handled. The balloons are easily removed from the manifold and are held in place by the elasticity of the balloon.

The present balloon contains three sections. A first section, the retainer section, at the open end of the balloon, is used as a stop for probe placement. This permits a repeatable placement of the probe in the ear canal. An intermediate section has a heavier wall than the inflatable section and will not inflate. It serves as an extension for the return flow of fluid. The inflatable section, at the closed end of the balloon, is very thin, assuring good heat transfer and the ability to conform to irregularities and shapes of different ear canals. The inflatable section has a slightly heavier wall at the tip, reducing the risk of damage during insertion and reducing the likelihood of breakage in the direction of the ear drum.

Briefly, the present probe includes a manifold and a balloon, the manifold conducting fluid flow into and out of the balloon concentrically, the balloon being a one-piece, elongate, cylindrical member formed from an elastic material and having open and closed ends and sections of different diameters and thicknesses, the balloon including a first, inflatable section defining the closed end thereof, the first section having a relatively small diameter to permit insertion into the ear canal and a minimum thickness to permit inflation thereof into contact with the inner ear, a second, non-inflatable section intermediate the open and closed ends thereof, the second section having a relatively small diameter to permit insertion into the ear canal and an increased thickness to prevent inflation thereof, the first and second sections being approximately equal in length, and a third, non-inflatable section defining the open end thereof, the third section having a relatively large outside diameter and a substantial thickness so as to contact the exterior ear and limit movement of the first and second sections of the balloon into the ear canal.

OBJECTS

It is therefore an object of the present invention to provide an ear probe for use in a closed-loop caloric irrigator for electronystagmography.

It is a further object of the present invention to provide an ear probe including a manifold and an inflatable balloon adapted to be placed in an ear canal.

It is a still further object of the present invention to provide an ear probe for use in a closed-loop caloric irrigator in which dimensions are held to a minimum and flow to a maximum.

It is another object of the present invention to provide an ear probe which permits maintenance of a precise temperature, close to or at the ear drum, regardless of the physical structure of a patient.

Still other objects, features and attendant advantages of the present invention will become apparent to those skilled in the art from a reading of the following detailed description of the preferred embodiment constructed in accordance therewith, taken in conjunction with the accompanying drawings wherein like numerals designate like parts in the several figures and wherein:

BRIEF DESCRIPTION OF THE DRAWINGS

FIg. 3 is a longitudinal sectional view of the probe of FIG. 1; and

FIG. 4 is a sectional view taken along the line 4—4 in FIG. 3.

DESCRIPTION OF THE PREFERRED EMBODIMENT

Figure 1:
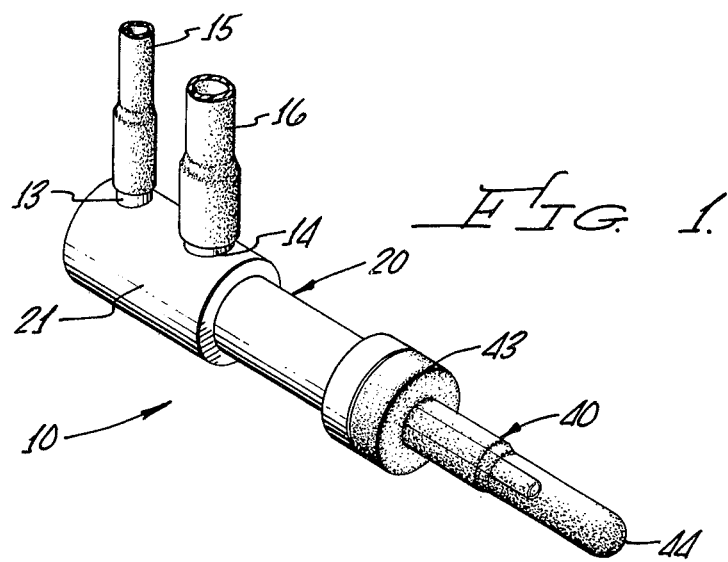
FIG. 1 is a perspective view of a probe constructed in accordance with the teachings of the present invention for use in a closed-loop caloric irrigator.

Referring now to the drawings, there is shown a probe, generally designated 10, for use with a caloric irrigator for unilateral or bilateral stimulation for use in ENG. For a complete description of a closed-loop caloric irrigator, which is not the subject of the present invention, reference should be had to my copending U.S. patent application Ser. No. 760,178, filed Jan. 17, 1977 and entitled Closed-Loop Caloric Irrigator.

For the purposes of the present invention, a caloric irrigator of the type described in my prior application includes a unitary cabinet having a front panel on which is mounted the various gauges and controls required. Such a caloric irrigator is of the general type previously described for pumping, for a predetermined time, a fluid, such as water, the temperature of which is accurately controlled, to probe 10 insertable in the ear canal 11 of a patient 12.

Housed within such unitary cabinet is a fluid reservoir which may consist simply of a cylindrical tank having at least one inlet and at least one outlet the outlet, of the reservoir being connected to the inlet of a pump, the operation of which is controlled by an electrical timer. Where the irrigator is designated for bilateral simultaneous stimulation, the output of the pump is typically connected to a conduit having four branches, each of which includes an identical valve, the valves being manually or electrically operated by switches mounted on the front panel of the cabinet. Two of the valves control the flow of fluid into a first heat exchanger for heating the fluid passing therethrough. The other two valves control the flow of fluid into a second heat exchanger for cooling the fluid passing therethrough.

In a caloric irrigator for bilateral simultaneous stimulation, two probes 10 would be utilized for effecting heat transfer between the fluid in the reservoir and the ear canals 11 of patient 12. Each probe 10 has an inlet 13 and an outlet 14. The inlets 13 of probe 10 are connected to the outlets of the heat exchangers by lengths of tubing 15. Outlets 14 are connected by lengths of tubing 16 to the inlets of the reservoir.

Generally speaking, the reservoir, the pump, the valves, the heat exchangers, and the probes are interconnected by means of conduit means, preferably plastic tubing, such as tubing 15 and 16, forming a closed-loop channel whereby the pump pumps fluid from the reservoir through one of the heat exchangers and the probes back to the reservoir. Whether hot or cold water is used is determined by which valves are opened and closed and which heat exchangers are used.

Referring now primarily to FIGS. 3 and 4, the construction of probe 10 will be described in detail. Specifically, probe 10 includes a manifold, generally designated 20, and a balloon, generally designated 40. Manifold 20 includes an elongate cylindrical body 21 having a central axial channel 22 therein. At one end of body 21, channel 22 is connected to a lateral channel 23 which receives one end of a sleeve 24 which provides the fluid inlet 13 for manifold 20. Sleeve 24 is connectable to fluid inlet line 15. Sleeve 24 conducts fluid from inlet line 15 into channel 23 and channel 22 and then into one end of an elongate sleeve 25 which terminates in channel 22 and extends through and out of the other end of body 21.

Adjacent the other end of body 21 is an enlarged axial channel 27 which is coaxial with channel 22 and has a diameter greater than the diameter of channel 22. Channel 27 is in fluid communication with a lateral channel 29 which receives one end of a sleeve 30 which functions as fluid outlet 14 of manifold 20. Sleeve 30 is connectable to fluid outlet line 16. Thus, sleeve 30 conducts fluid from channel 27 into fluid outlet line 16.

Channel 27 receives one end of an elongate sleeve 31 which is coaxial with sleeve 25, sleeve 25 extending entirely through sleeve 31 which extends slightly beyond the other end of body 21. The outside diameter of sleeve 25 is less than the inside diameter of sleeve 31 to permit fluid flow therebetween. The end of sleeve 25 which extends beyond body 21 of manifold 20 receives one end of an elastic tube extension 32 which is preferably made from silicone, for reasons which will appear more fully hereinafter.

According to the present invention, probe 10 incorporates balloon 40 which is preferably made from silicone rubber so as to be highly elastic and capable of repeated cycles of expansion and contraction. Balloon 40 is designed so that probe 10 may maintain a precise temperature, for a given time, in ear canal 11, as close to ear drum 17 of patient 12 as possible. For sterilization purposes, balloon 40 is readily removable from manifold 20 so that balloon 40 can be discarded.

More specifically, balloon 40 is a one-piece, elongate, cylindrical member having an open end and a closed end. Preferably, balloon 40 has a uniform inside diameter throughout the length thereof and includes sections 41, 42, and 43 of different outside diameters and different thicknesses. Section 41 of balloon 40 is the inflatable balloon section which defines the closed end of balloon 40. Section 41 has a relatively small outside diameter to permit insertion into ear canal 11. Section 41 also has a minimum thickness to permit inflation thereof into contact with the inner ear. This assures good heat transfer and also ensures that balloon section 41 will conform to the irregularities and shapes of ear canal 11.

On the other hand, balloon section 41 has a slightly increased wall thickness at the tip 44 thereof to reduce the risk of damage during insertion into ear canal 11 and making it less likely that balloon section 41 will break in the direction of ear drum 17. According to the present invention, balloon section 41 preferably has an inside diameter of 3.7 mm, a wall thickness of 0.15 mm, an outside diameter of 4 mm, and a length of 13 mm.

The open end of inflatable section 41 is integral with a shaft section 42 which is non-inflatable and positioned intermediate the open and closed ends of balloon 40. Section 42 has a relatively small diameter to permit insertion into ear canal 11 but an increased wall thickness to prevent inflation thereof. Section 42 serves as an extension for the return flow of fluid through balloon section 41. If the thicknesses of sections 41 and 42 were the same, it would be very likely that section 42 would inflate outside of ear canal 11 and break. As can be seen from an inspection of FIG. 2, section 42 does not inflate, all the inflation of balloon 40 being in section 41. According to the present invention, section 42 preferably has an inside diameter of 3.7 mm, a wall thickness of 0.4 mm, an outside diameter of 4.5 mm, and a length of 13 mm. It can therefore be seen that the lengths of sections 41 and 42 are approximately equal, again ensuring that there is no inflation of balloon 41 outside of ear canal 11.

Figure 2:
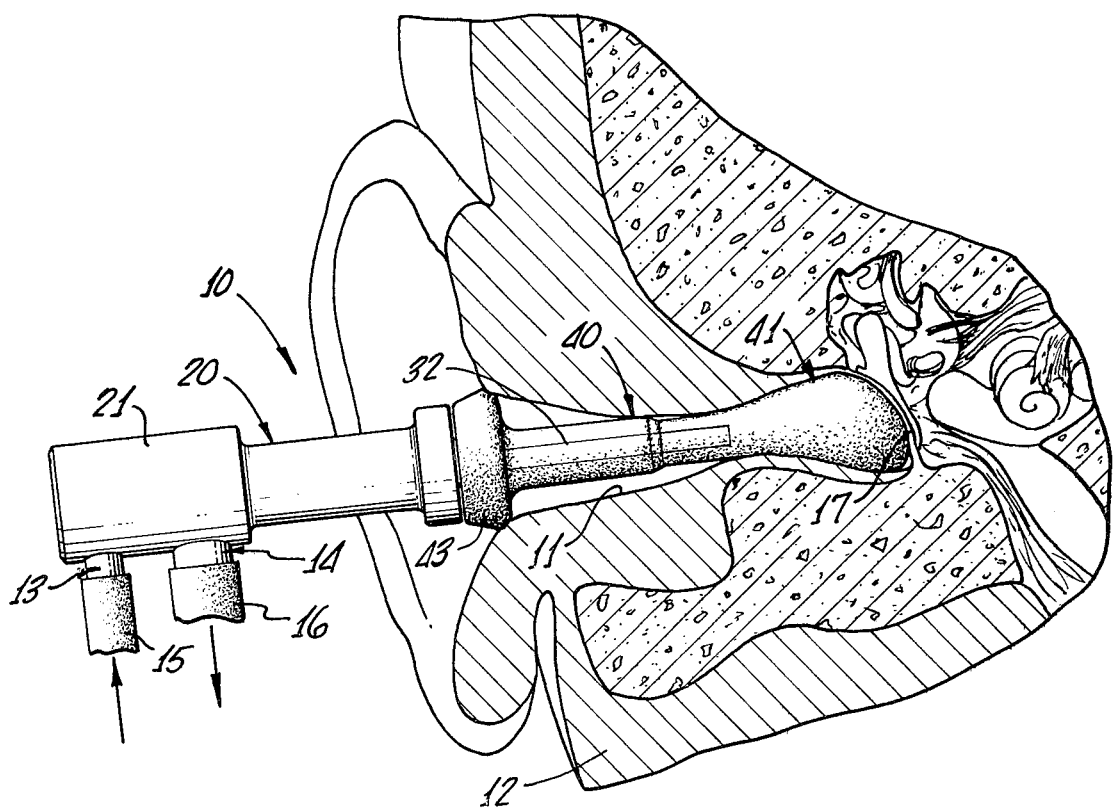
FIG. 2 is a side elevation view of the probe of FIG. 1 shown in operative, inflated position in the ear canal.

Balloon 40 includes a third, non-inflatable, retainer section 43 defining the open end thereof, retainer section 43 having a relatively large outside diameter and a substantial thickness so as to function as a stop for proper placement. That is, as shown in FIG. 2, the outside diameter of retainer section 43 is such that it will contact the exterior ear and limit movement of sections 41 and 42 of balloon 40 into ear canal 11. Since total heat transfer is dependent on balloon contact, it is important that placement in ear canal 11 be repeatable and retainer section 43 ensures that this is the case. Furthermore, retainer section 43 may be fitted onto sleeve 31 of manifold 20 and is held in position thereat by the elasticity of the material of balloon 40. According to the present invention, section 43 preferably has an inside diameter of 3.7 mm, an outside diameter of 9.5 mm, and a length of 4 mm.

As can be seen in FIGS. 2 and 3, tube extension 32 assures a good liquid delivery close to tip 44 of inflatable section 41 where irrigation is most important. Furthermore, when inserting probe 10 into ear canal 11, extension 32 prevents balloon 40 from doubling over.

As will be apparent from an inspection FIG. 3, fluid conducted to manifold 20 by inlet line 15 flows through sleeve 25 and extension 32 into inflatable section 41 of balloon 40. Such fluid then passes between tube extension 32 and shaft section 42 of balloon 40, between sleeves 25 and 31, and through channel 27 and flows via sleeve 30 into fluid outlet line 16.

It can therefore be seen that according to the present invention, the problems encountered with previous probes for use in a closed-loop caloric irrigator are solved by the provision of a unique probe 10. Probe 10 includes a manifold 20 and an inflatable balloon 40 adapted to be placed in ear canal 11 and to have a fluid such as water pumped therethrough for stimulating ear canal 11. With probe 10, the fluid flow into and out of balloon 40 is concentric. This allows sections 41 and 42 of balloon 40 to have a small diameter, providing greater applicability with individuals with small or partially obstructed ear canals. Probe 10 is not only smaller, but simpler and less costly than prior designs, permitting replacement of balloon 40 only and not the entire probe 10. Use of a concentric in-flow and out-flow system also prevents partial collapse of balloon 40 because of the ear creating a restriction.

Probe 10 is soft and of low mass so that placement can be made with the least amount of trauma to a patient. The hoses leading to manifold 20 are small and lightweight and are attached to body 21 at a right angle to assure a minimal total mass to be handled. Balloon 40 is easily removable from manifold 20 and is held in place by the elasticity of balloon 40.

While the invention has been described with respect to the preferred physical embodiment constructed in accordance therewith, it will be apparent to those skilled in the art that various modifications and improvements may be made within departing from the scope and spirit of the invention. Accordingly, it is to be understood that the invention is not to be limited by the specific illustrative embodiment, but only by the scope of the appended claims.

I claim:
1. An ear canal balloon comprising:
   a one-piece, elongate, cylindrical member formed from an elastic material and having open and closed ends and sections of different diameters and thicknesses, said member including:
   a first section defining the closed end thereof, said first section having a relatively small diameter to permit insertion into an ear canal and a minimum thickness to permit inflation thereof into contact with the inner ear;

a second section intermediate the open and closed ends thereof, said second section having a relatively small diameter to permit insertion into said ear canal and a thickness which is greater than the thickness of said first section by an amount sufficient to prevent inflation thereof in use, said first and second sections being approximately equal in length; and a third section defining the open end thereof, said third section having a relatively large outside diameter and a substantial thickness so as to contact the exterior ear and limit movement of said first and second sections of said balloon into said ear canal.

2. An ear balloon according to claim 1, wherein said member is made from silicone rubber.

3. An ear balloon according to claim 1 or 2, wherein said first, second and third sections have the same inside diameter.

4. An ear balloon according to claim 1, wherein said first section has a slightly increased wall thickness at the tip thereof.

5. An ear balloon according to claim 1, wherein said first section has an inside diameter of approximately 3.7 mm and a wall thickness of approximately 0.15 mm.

6. An ear balloon according to claim 5, wherein said second section has an inside diameter of approximately 3.7 mm and a wall thickness of approximately 0.4 mm.

7. An ear balloon according to claim 6, wherein said third section has an inside diameter of approximately 3.7 mm and an outside diameter of approximately 9.5 mm.

8. An ear balloon according to claim 7, wherein said first, second, and third sections have lengths of approximately 13 mm, 13 mm, and 4 mm, respectively.

9. An ear probe for use in closed-loop caloric irrigation comprising:
a manifold including:
an elongate cylindrical body having a side wall, an open end and a closed end and first and second coaxial channels extending therethrough; and
inlets and outlets extending laterally through said side wall of said body into fluid communication with said first and second channels, respectively; and a one-piece, elongate, cylindrical, ear canal balloon formed from an elastic material and having open and closed ends and sections of different diameters and thicknesses, said open end of said balloon being removably connectable to said open end of said manifold body, said manifold conducting fluid into and out of said balloon.

10. An ear probe according to claim 9, wherein said manifold body has a central axial channel connected to said outlet and a sleeve extending through said channel and connected to said inlet, said open end of said balloon being connected to said body of said manifold and said sleeve extending into said balloon.

11. An ear probe according to claim 9 or 10, wherein said balloon comprises:

a first section defining the closed end thereof, said first section having a relatively small diameter to permit insertion into an ear canal and a minimum thickness to permit inflation thereof into contact with the inner ear;

a second section intermediate the open and closed ends thereof, said second section having a relatively small diameter to permit insertion into said ear canal and a thickness which is greater than the thickness of said first section by an amount sufficient to prevent inflation thereof in use, said first and second sections being approximately equal in length; and a third section defining the open end thereof, said third section having a relatively large outside diameter and a substantial thickness so as to contact the exterior ear and limit movement of said first and second sections of said balloon into said ear canal.

* * * * *